(12) United States Patent
Chang et al.

(10) Patent No.: US 8,372,951 B2
(45) Date of Patent: Feb. 12, 2013

(54) CELL PENETRATING PEPTIDES FOR INTRACELLULAR DELIVERY

(75) Inventors: Margaret Dah-Tsyr Chang, Hsinchu (TW); Shun-Lung Fang, Hsinchu (TW); Wei-I Chou, Hsinchu (TW); Shu-Chuan Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 263 days.

(21) Appl. No.: 12/780,497

(22) Filed: May 14, 2010

(65) Prior Publication Data

US 2011/0280798 A1    Nov. 17, 2011

(51) Int. Cl.
*C07K 7/00* (2006.01)
*C07K 7/06* (2006.01)
*A61K 38/00* (2006.01)
*A61K 38/08* (2006.01)

(52) U.S. Cl. .......................... 530/328; 530/300; 514/1.2
(58) Field of Classification Search .................. None
See application file for complete search history.

(56) References Cited

U.S. PATENT DOCUMENTS

| | | | | |
|---|---|---|---|---|
| 7,029,899 B1 * | 4/2006 | Rybak et al. | ................... | 435/199 |
| 7,595,374 B1 * | 9/2009 | Chang et al. | ................... | 530/330 |
| 2010/0016239 A1 * | 1/2010 | Chang et al. | .................... | 514/14 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

* cited by examiner

*Primary Examiner* — Julie Ha
(74) *Attorney, Agent, or Firm* — WPAT, P.C.; Anthony King

(57) ABSTRACT

A cell penetrating peptide which has following sequence: $NYBX_1BX_2BNQX_3$, wherein B represents a basic amino acid, $X_1$ represents an amino acid with an aromatic, a hydrophobic or an uncharged side chain, $X_2$ represents any amino acid, and $X_3$ represents N or none is described. A method for delivering a cargo into a subject by administrating a complex comprising the cell penetrating peptide and the desired cargo to the subject is also described.

5 Claims, 8 Drawing Sheets

A.

B.

| Sample | MFI |
|---|---|
| FITC | 4.54±0.89 |
| ECP (32-41)  20 µM | 101.79±2.27 |

FITC

ECP(32-41)

ECP(32-41) D1

ECP(32-41) D2

| Sample | MFI |
|---|---|
| FITC | 2.85 ± 1.33 |
| Dp2 5 µM | 3.98 ± 1.96 |
| Dp2-ECP (32-41) 5 µM | 54.18 ± 3.61 |

| Sample | MFI |
|---|---|
| Control | 2.56±0.23 |
| eGFP | 5.45±2.26 |
| eGFP-ECP(32-41) | 15.32±2.03 |

A.

B.

C.

A.

B.

CELL PENETRATING PEPTIDES FOR INTRACELLULAR DELIVERY

FIELD OF THE INVENTION

The present invention pertains to the field of intracellular delivery of molecules such as proteins or nucleic acids. In particular, the invention relates to a new cell penetrating peptide (CPP) derived from eosinophil cationic protein (ECP), which exhibits highly cell-penetrating efficiency and low toxicity.

BACKGROUND OF THE INVENTION

Cellular internalization of large hydrophilic therapeutic agents such as proteins or nucleic acids is still a challenging task because of the presence of plasma membrane, which constitutes an impermeable barrier for such molecules. In order to circumvent this problem, several methods of carrier-mediated delivery systems have been developed. Among them, much attention has recently been given to the use of peptide-based delivery systems. The use of peptides with cell-penetrating properties has several advantages, which are mainly due to various modifications that can be done to the peptide sequence. This allows the engineering of carriers addressing different cellular subdomains and/or is able to transport various types of cargos. Cell penetrating peptides (CPPs) such as antennapedia-derived penetratin (Derossi, D., Joliot, A. H., Chassaing, G., and Prochiantz, A. (1994) *J Biol Chem* 269, 10444-50) and HIV Tat peptide (Vives, E., Brodin, P., and Lebleu, B. (1997) *J Biol Chem* 272, 16010-7) are widely used tools for the delivery of peptides, proteins and oligonucleotides into cells (Fischer, P. M., Krausz, E., and Lane, D. P. (2001) *Bioconjug Chem* 12, 825-41). Areas of application range from cell biology (Jarver, P., Langel, K., El-Andaloussi, S., and Langel, U. (2007) *Biochem Soc Trans* 35, 770-4) to biomedical research (Foerg, C., and Merkle, H. P. (2008) *J Pharm Sci* 97, 144-62). Immunological relevance of CPPs is crucial to biomedical research. Nevertheless, most CPPs used to date are of non-human origin and therefore an adaptive immune response may be induced, especially when conjugated to proteins and nanoparticles. Therefore, CPPs like the human calcitonin-derived peptide (Ding, G. J., Fischer, P. A., Boltz, R. C., Schmidt, J. A., Colaianne, J. J., Gough, A., Rubin, R. A., and Miller, D. K. (1998) *J Biol Chem* 273, 28897-905) and peptides corresponding to signal sequences of human proteins (Rojas, M., Donahue, J. P., Tan, Z., and Lin, Y. Z. (1998) *Nat Biotechnol* 16, 370-5) are being considered as highly attractive import vehicles.

Human eosinophil cationic protein (ECP) secreted by activated eosinophil granules possesses 133 amino acids with an isoelectric point (pI) of 10.8 (Venge, P., Bystrom, J., Carlson, M., Hakansson, L., Karawacjzyk, M., Peterson, C., Seveus, L., and Trulson, A. (1999) *Clin Exp Allergy* 29, 1172-86) and a molecular weight ranging from 16 to 22 kDa as a result of different glycosylation extent (Venge, P., Bystrom, J., Carlson, M., Hakansson, L., Karawacjzyk, M., Peterson, C., Seveus, L., and Trulson, A. (1999) *Clin Exp Allergy* 29, 1172-86). ECP possesses antibacterial activity (Rosenberg, H. F. (1995) *J Biol Chem* 270, 7876-81) against Gram-positive bacteria such as *Staphylococcus aureus* (*S. aureus*) and Gram-negative bacteria including *Escherichia coli* (*E. coli*) (Rosenberg, H. F. (1995) *J Biol Chem* 270, 7876-81). Besides bactericidal activity, ECP also has helminthotoxic (Hamann, K. J., Gleich, G J., Checkel, J. L., Loegering, D. A., McCall, J. W., and Barker, R. L. (1990) *J Immunol* 144, 3166-73) and antiviral (Domachowske, J. B., Dyer, K. D., Adams, A. G, Leto, T. L., and Rosenberg, H. F. (1998) *Nucleic Acids Res* 26, 3358-63) activities against respiratory syncytial virus (RSV). It has been proven that synthetic ECP(1-45) peptide reproduces most of ECP's antimicrobial properties and the ECP (24-45) segment is essential for antimicrobial activity (Torrent, M., de la Torre, B. G, Nogues, V. M., Andreu, D., and Boix, E. (2009) *Biochem J* 421, 425-34). We have previously reported that cell surface glycosaminoglycan (GAGs), especially heparan sulfate proteoglycans (HSPGs) promotes internalization of ECP via macropinocytosis pathway (Fan, T. C., Chang, H. T., Chen, I. W., Wang, H. Y., and Chang, M. D. (2007) *Traffic* 8, 1778-95). The cytotoxicity of ECP was severely reduced toward the mutant cell lines deficient in heparan sulfate (HS) (Fan, T. C., Chang, H. T., Chen, I. W., Wang, H. Y., and Chang, M. D. (2007) *Traffic* 8, 1778-95). Our results indicate that the motif containing charged and aromatic residues located within the region ECP(34-38) modulates the interaction between ECP and heparin (Fan, T. C., Fang, S. L., Hwang, C. S., Hsu, C. Y., Lu, X. A., Hung, S. C., Lin, S. C., and Chang, M. D. (2008) *J Biol Chem* 283, 25468-74). The motif has also been disclosed in the U.S. Pat. No. 7,595,374.

In addition, it has been demonstrated that antimicrobial peptides and CPPs possess concordant functional characteristics. For example, Magainin 2 from the skin of the South-African clawed frog *Xenopus laevis* is taken up into mammalian cells (Takeshima, K., Chikushi, A., Lee, K. K., Yonehara, S., and Matsuzaki, K. (2003) *J Biol Chem* 278, 1310-5) and shows antimicrobial activity (Nekhotiaeva, N., Elmquist, A., Rajarao, G K., Hallbrink, M., Langel, U., and Good, L. (2004) *FASEB J* 18, 394-6). In the present invention, the biological function and potential application of a novel CPP derived from ECP which contains a heparin binding motif are disclosed.

BRIEF DESCRIPTION OF THE DRAWINGS

FIG. 5 illustrates in vitro delivery of peptide. Beas-2B cells were incubated with 5 μM FITC (control), FITC-Dp2 or FITC-Dp2-ECP(32-41) at 37° C. for 1 h. After treatment, cells were washed with 500 μl PBS and treated with trypsin at 37° C. for 10 min to remove adherent extracellular peptides. The cells were resuspended in 500 μl PBS and analyzed by flow cytometry. The cellular uptake activity was expressed as mean fluorescence intensity (MFI) using FACScalibur (BD Biosciences, Franklin Lakes, N.J.) flow cytometer (FACS). The data represented the means of triplicate incubations.

SUMMARY OF THE INVENTION

Figure 1:
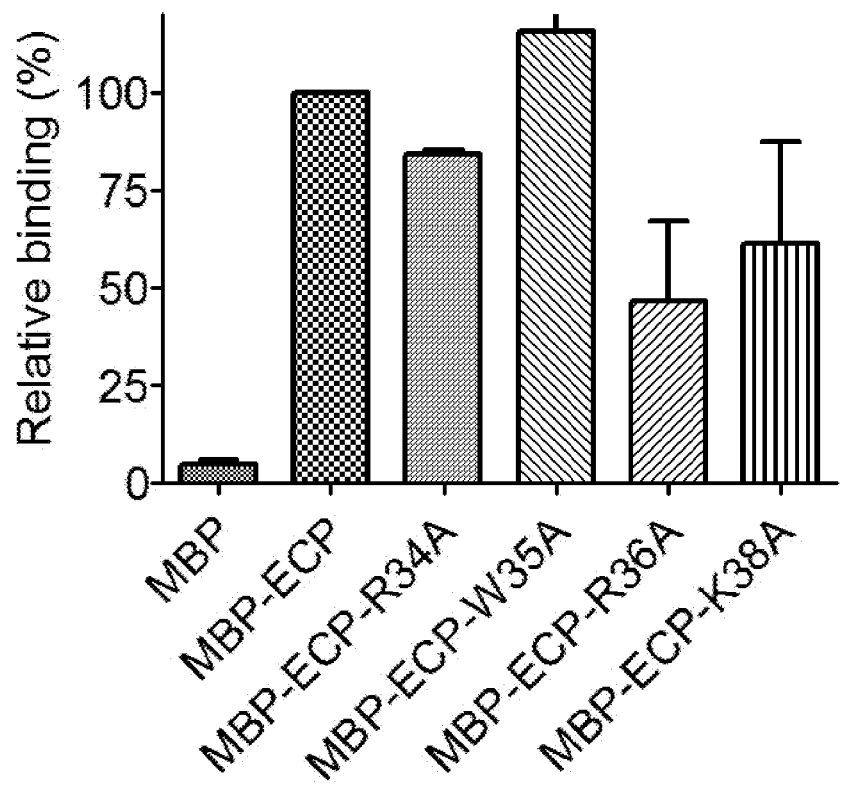
FIG. 1 illustrates relative binding activity of wild type and mutant MBP-ECP to Beas-2B cells. (A) R34A, W35A, R36A and K38A. (B) R34K, W35F, W35Y, R36K and K38R. Beas-2B cells were treated with various MBP-ECP derivatives carrying single point mutation in RPMI-1640 medium at 4° C. for 1 h. The cells were washed with PBS and fixed by PFA. The amount of MBP-ECP derivatives bound to cells was assayed by ELISA. MBP-ECP (800 nM) was used as the positive control set of 100 percent binding and the relative binding affinities for the MBP-ECP derivatives were calculated. The data represented the means of triplicate incubations. The error bars showed standard deviations among triplicate experiments.
Figure 1:
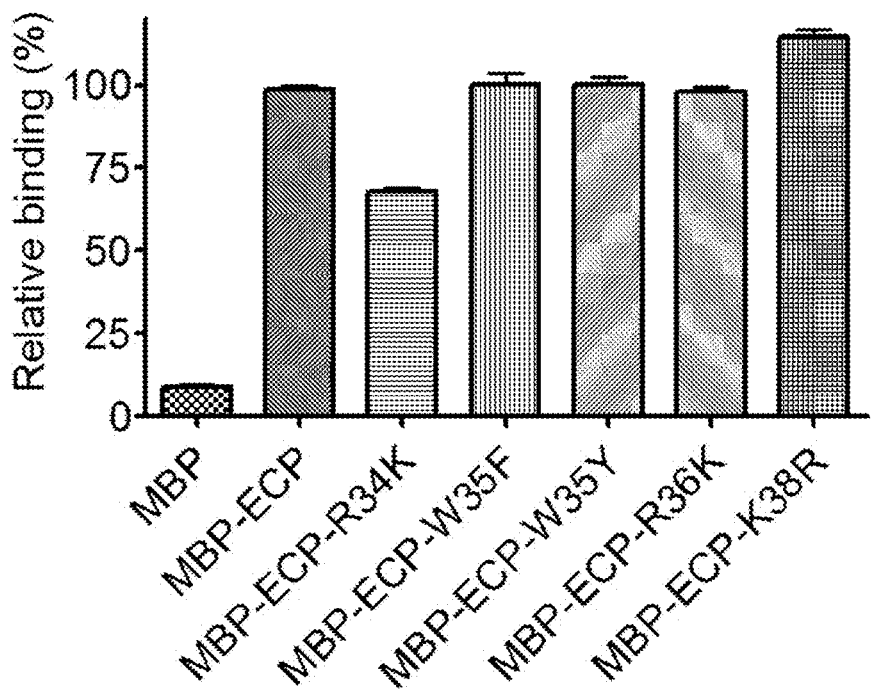

The present invention provides a cell penetrating peptide which has following sequence: NYBX$_1$BX$_2$BNQX$_3$, wherein B represents a basic amino acid, X$_1$ represents an amino acid with an aromatic, a hydrophobic or an uncharged side chain, X$_2$ represents any amino acid, and X$_3$ represents N or none.

The present invention further provides a method of intracellular delivery comprising: (a) providing a cell penetrating peptide of the present invention, and (b) incubating the cell penetrating peptide with targeted cells.

The present invention also provides a complex comprising the cell penetrating peptide of the present invention and a cargo selected from the group consisting of therapeutic agents, diagnostic probes, peptides, nucleic acids, antisense oligonucleotides, proteins, nanoparticles, liposomes, small molecules and radioactive materials.

The present invention further provides a method for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject.

DETAILED DESCRIPTION OF THE INVENTION

The present invention provides a cell penetrating peptide which has following sequence: NYBX$_1$BX$_2$BNQX$_3$, wherein B represents a basic amino acid, X$_1$ represents an amino acid with an aromatic, a hydrophobic or an uncharged side chain, preferably W, A, F, Y, or H; X$_2$ represents any amino acid, and X$_3$ represents N or none. In a preferable embodiment, B represents R, X$_1$ represents W, A, F, or Y, and X$_2$ represents C. In another preferable embodiment, the cell penetrating peptide is SEQ ID NO: 1 or SEQ ID NO: 2. In a more preferable embodiment, the cell penetrating peptide is SEQ ID NO: 1.

In one aspect of the present invention, the cell penetrating peptide further comprises a cargo. The term "cargo" used herein includes but is not limited to the group consisting of therapeutic agents, diagnostic probes, peptides, nucleic acids, antisense oligonucleotides, proteins, nanoparticles, liposomes, small molecules and radioactive materials.

The terms "antisense oligonucleotides" or "antisense compound" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid: oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence; variations in sequence near the termini of an oligomer are generally preferable to variations in the interior.

The present invention also provides a method of intracellular delivery comprising: (a) providing a cell penetrating peptide of NYBX$_1$BX$_1$BNQX$_2$, wherein B represents a basic amino acid, X$_1$ represents an amino acid with an aromatic, a hydrophobic or an uncharged side chain, preferably W, A, F, Y, or H; X$_2$ represents any amino acid, and X$_3$ represents N or none; and (b) incubating the cell penetrating peptide with targeted cells. In a preferable embodiment, the cell is pulmonary, ovary, gastric or intestinal cells. In a preferable embodiment, the cell penetrating peptide further comprises a cargo selected from the group consisting of therapeutic agents, diagnostic probes, peptides, nucleic acids, antisense oligonucleotides, proteins, nanoparticles, liposomes, small molecules and radioactive materials.

The present invention further provides a complex comprising the cell penetrating peptide of the present invention and a cargo selected from the group consisting of therapeutic agents, diagnostic probes, peptides, nucleic acids, antisense oligonucleotides, proteins, nanoparticles, liposomes, small molecules and radioactive materials, wherein the cargo is preferably selected from the group consisting of chromophores, peptides and proteins. In one particular aspect, the invention pertains to the use of a cell penetrating peptide, or of the complex as described above, for the preparation of a pharmaceutical composition for use in therapy and scientific research.

The present invention provides a method for delivering a cargo into a subject comprising: (a) preparing a complex comprising the cell-penetrating peptide of the present invention and a cargo selected from the group consisting of therapeutic agents, diagnostic probes, peptides, nucleic acids, antisense oligonucleotides, proteins, nanoparticles, liposomes, small molecules and radioactive materials, wherein the cargo is preferably selected from the group consisting of chromophores, peptides and proteins, and (b) orally, intraarticularly, intraperitoneally, intrathecally, intrarterially, intranasally, intraparenchymally, subcutaneously, intramuscularly, intravenously, dermally, intrarectally, or topically administering the complex to a subject, wherein the subject is a vertebrate, or more specifically, a zebrafish. In a preferable embodiment, the cargo is preferably selected from the group consisting of chromophores, peptides and proteins.

EXAMPLE

The examples below are non-limiting and are merely representative of various aspects and features of the present invention.

Example 1

Identification of Specific Heparin Binding Residues in ECP(32-41)

Cell Culture

Beas-2B cells were cultured in RPMI 1640 medium (Gibco, Invitrogen, USA) supplemented with heat-inactivated 10% (v/v) fetal bovine serum (FBS) (Gibco, Invitrogen, USA), and 1% (v/v) Glutamine-Penicillin-Streptomycin (biosera). Cells were grown on 100-mm dishes and incubated at 37° C. under 5% $CO_2$.

Protein Expression and Purification

For cell-binding assays, pMAL-c2G expression and purification system (New England Biolabs) was chosen for recombinant ECP fused with N-terminal maltose binding protein (MBP) between the EcoRI and XbaI site and expressed in soluble form in *E. coli*. Amino acid residues R34, W35, R36, and K38 of ECP were individually substituted with other amino acids using QuickChange site-directed mutagenesis (Stratagene) with primer pairs, 5'-GCAATTAACAATTATGCATGGCGTTGCAAAAACC-3' (SEQ ID NO: 8)/5'-GGTTTTTGCAA CGCCATGCATAATTGTTAATTGC-3' (SEQ ID NO: 9) (R34A), 5'-GCAATTAACAATTATAAATGGCGTTGCAAAAACC-3' (SEQ ID NO: 10)/5'-GGTTTTTGCAACGCCATTTATAATTGTTAATTGC-3' (SEQ ID NO: 11) (R34K), 5'-ATTAACAATTATCGAGCGCGTTGCAAAAACC-3' (SEQ ID NO: 12)/5'-GGTTTTTG CAACGCGCTCGATAATTGTTAAT-3' (SEQ ID NO: 13) (W35A), 5'-ATTAACAATTATCGATTTCGTTGCAAAAACC-3' (SEQ ID NO: 14)/5'-GGTTTTTGCAACGAAATCGATAATTGTTAAT-3' (SEQ ID NO: 15) (W35F), 5'-ATTAACAATTATCGATCTCGTTGCAAAAACC-3' (SEQ ID NO: 16)/5'-GGTTTTTG-CAACGAGATCGATAATTGTTAAT-3' (SEQ ID NO: 17) (W35Y), 5'-CAATTATCGATGGGCTTGCAAAAAC-CAAAATAC-3' (SEQ ID NO: 18)/5'-GTATTTTG-GTTTTTGCAAGCCCATCGATAATTG-3' (SEQ ID NO: 19) (R36A), 5'-CAATTATCGATGGAAATGCAAAAAC-CAAAATAC-3' (SEQ ID NO: 20)/5'-GTATTTTG-GTTTTTGCAATTTCATCGATAATTG-3' (SEQ ID NO: 21) (R36K), 5'-TATCGATGGCGTTGCGCAAAC-CAAAATACT-3' (SEQ ID NO: 22)/5'-AAAGTATTTTG-GTTTGCGCAACGCCATCGAT-3' SEQ ID NO: 23) (K38A), and 5'-TATCGATGGCGTTGCAAAAAC-CAAAATACT-3' (SEQ ID NO: 24)/5'-AAAGTATTTTG-GTTTTTGCAACGCCATCGAT-3' (SEQ ID NO: 25 (K38R). *E. coli* BL21 (DE3) Codon Plus (Novagen, Calif.) competent cells were prepared by calcium chloride method and were used for transformation of various plasmids. Recombinant wild type MBP-ECP and its single-point mutation derivatives were expressed upon IPTG induction and purified using affinity chromatography as previously described (Fan, T. C., Chang, H. T., Chen, I. W., Wang, H. Y., and Chang, M. D. (2007) *Traffic* 8, 1778-95).

Cell Enzyme-Link Immunosorbent Assay (Cell ELISA)

Beas-2B were seeded at a density of $2\times10^4$ cells/well onto a 96-well black plate, and incubated at 37° C. and 5% $CO_2$ for 24 h. Beas-2B cells in 96-well plates were treated with various concentrations of wild type or mutant MBP-ECP at 4° C. for 1 h. The cells were then washed with ice-cold PBS and fixed with 2% PFA for 15 min at room temperature prior to blocking with 2% BSA/PBS at room temperature for 90 min. The detection was conducted using an enhanced chemiluminescence (ECL) detection system and the signal intensity correlates to the amount of bound target protein. MBP-ECP was detected using mouse monoclonal anti-MBP antibody, and goat anti-mouse IgG-HRP conjugate was added as secondary antibody.

The ECP(32-41) comprising the exposed loop L3 region of ECP serves as the specific binding site for heparin (Fan, T. C., Chang, H. T., Chen, I. W., Wang, H. Y., and Chang, M. D. (2007) *Traffic* 8, 1778-95). To characterize the sequence dependence of the heparin binding motif, Beas-2B cells were incubated with wild type MBP-ECP or its single-point mutation derivatives at different concentration (200, 400, 600 and 800 nM) at 4° C. for 1 h, and the luminescence was detected at $\lambda_{ex}$=570 nm. The mean value measured bound to Beas-2B cells from 800 nM wild type MBP-ECP treatment was set to 100%, and the other values were given in reference to this accordingly. Relative binding abilities of wild type and mutant MBP-ECP to Beas-2B cells were illustrated in FIG. 1. Alanine scanning mutagenesis was used to identify the amino acid residues essential for the binding with heparin. R34A, R36A and R38A mutants showed a decreased ability to bind Beas-2B cells, indicating that these positively charged residues were important (FIG. 1A). Furthermore, substitution with similar charged-residue including R34K, R36K and K38R mutant MBP-ECP showed similar binding abilities to Beas-2B cells (FIG. 1B), strongly suggesting that these positively charged residues involved in molecular interaction with heparin and were required and interchangeable at these positions. To determine if the aromatic amino acid at position 35 of ECP was essential for heparin binding, it appeared that the single-point mutation W35F or W35Y were still able to bind to Beas-2B cells (FIG. 1B). The Trp35 could be replaced with other residues including Tyr, Phe, and Ala (FIG. 1A), suggesting that a variety of mutations were tolerable at this position. Taken together, the heparin binding motif of ECP could be defined as a consensus sequence: BXBXB, which is comprised of basic (B) and hydrophobic or uncharged (X) amino acid residues.

Example 2

Cell Penetration of ECP (32-41)

Flow Cytometry

Cells ($2.0\times10^5$ cells/well) were plated into a 6-well microplate and cultured for 24 h in RPMI 1640 medium containing 10% heat-inactivated bovine serum (Beas-2B). After complete adhesion, the cells were incubated at 37° C. with fluorescence-labeled peptides dissolved in fresh serum-containing medium prior to washing with PBS. The cells were then treated with 0.25% trypsin at 37° C. for 10 min prior to addition of PBS, and centrifuged at 300×g for 5 min at 4° C. The supernatant was removed and the cells were washed with PBS and centrifuged at 300×g for 5 min at 4° C. The washing cycle was repeated again and the cells were suspended in PBS and subjected to fluorescence analysis on a FACScalibur (BD Biosciences, Franklin Lakes, N.J.) flow cytometer (FACS) using 488-nm laser excitation and a 515-545-nm emission filter.

Figure 2:
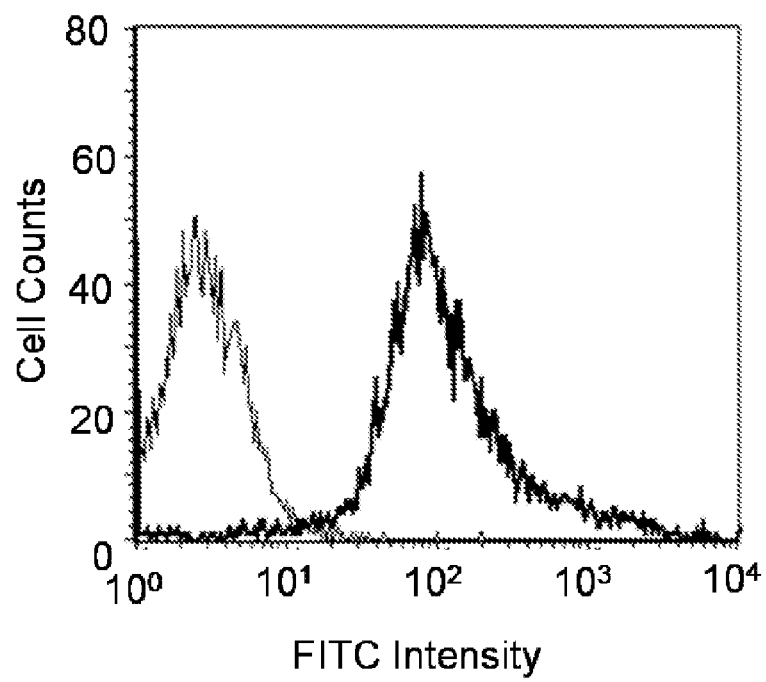
FIG. 2 illustrates cellular uptake of ECP(32-41). Beas-2B cells were incubated with 20 μM FITC (control) or FITC-ECP(32-41) at 37° C. for 30 min. After treatment, the cells were washed with 500 μl phosphate buffered saline (PBS) and treated with trypsin at 37° C. for 10 min to remove adherent extracellular peptides. The cells were resuspended in 500 μl PBS and analyzed by flow cytometry. The cellular uptake activity was expressed as mean fluorescence intensity (MFI) using FACScalibur (BD Biosciences, Franklin Lakes, N.J.) flow cytometer (FACS). The data represented the means of triplicate incubations.

Flow cytometric analysis was used to quantify cellular association of fluorochrome-tagged peptide, FITC-ECP(32-41) (SEQ ID NO: 1). To allow assessment of peptide translocation, Beas-2B cells were treated with 20 μM FITC (control) or FITC-ECP(32-41) at 37° C. for 30 min. The extracellular fluorescence of surface bound FITC-ECP(32-41) was subsequently removed by trypsinization. The cells were then detached with trypsin, centrifuged, and washed before flow cytometry analyses. The result showed significant uptake of FITC-ECP(32-41) in Beas-2B cells as evidenced by apparent fluorescent signal shift (FIG. 2).

Example 3

Intracellular Distribution of ECP(32-41)

Confocal Microscopy

Cells (1.0×10⁴ cells/well) were plated on 18-mm glass-bottomed dishes (Marienfeld, Germany) and cultured in medium containing 10% heat-inactivated fetal bovine serum for 24 h. After complete adhesion, the cell culture medium was removed, and then incubated at 37° C. in fresh medium containing the fluorescence-labeled peptides. The cells were washed with PBS, then fixed by 2% (w/v) paraformaldehyde (PFA) in PBS for 15 min, and 50 mM ammonium chloride in PBS was added to quench with fluoresce from PFA. Distribution of the fluorescence-labeled peptides in the cells was analyzed using a confocal scanning laser microscope (Zeiss).

Figure 3:
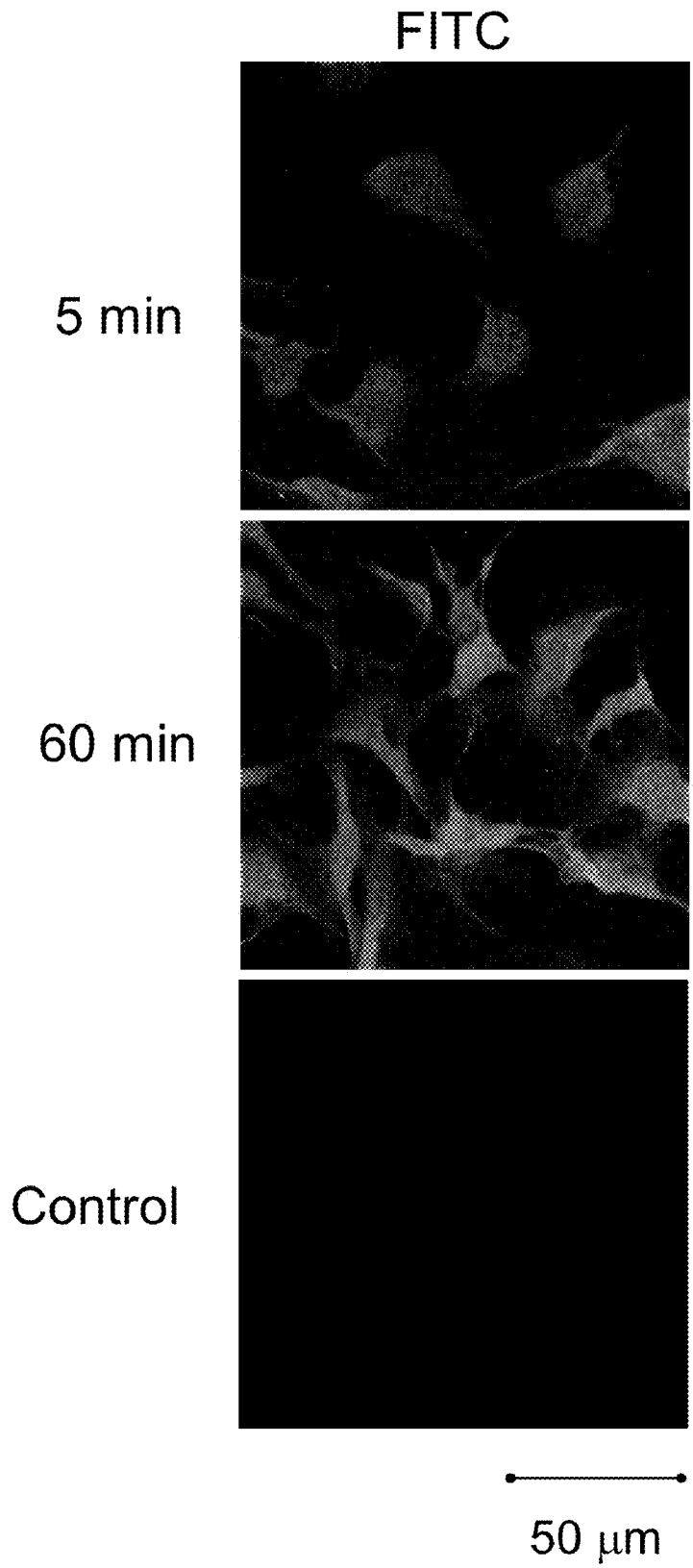
FIG. 3 illustrates intracellular distribution of cell-penetrating ECP(32-41). Beas-2B cells were incubated with 5 μM FITC-ECP(32-41) at 37° C. for 5 or 60 min. After wash with 1 ml PBS buffer twice, the cellular uptake was analyzed by confocal laser scanning microscopy. Magnification ford: 63×. Scale bar: 50

The intracellular localization of the FITC-ECP(32-41) in Beas-2B cells was investigated by confocal microscopy. Upon treatment with 5 μM FITC-ECP (32-41) for 5 min, a clear fluorescence signal inside the cells was observed, indicating that the ECP(32-41) entered the cells efficiently. Stronger signal was visible when cells were treated FITC-ECP(32-41) up to 60 min. As shown in FIG. 3, intracellular ECP(32-41) localization was observed in both cytoplasm and nucleus. The uptake studies of ECP(32-41) indicated that the translocation process occurred in a time- and concentration-dependent manner.

Example 4

Length Dependence of ECP(32-41) for Efficient Uptake

Figure 4:
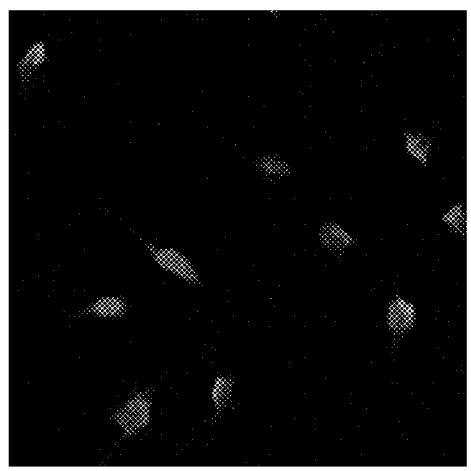
FIG. 4 illustrates minimal length requirement of cell penetration peptide. Beas-2B cells were incubated with 5 μM FITC-ECP(32-41), FITC-ECP(32-41)D1, and FITC-ECP (32-41)D2 separately at 37° C. for 30 min. After wash with 1 ml PBS buffer twice, the cellular uptake was analyzed by confocal laser scanning microscopy. Magnification fold: 40×. Scale bar: 50
Figure 4:
Figure 4:
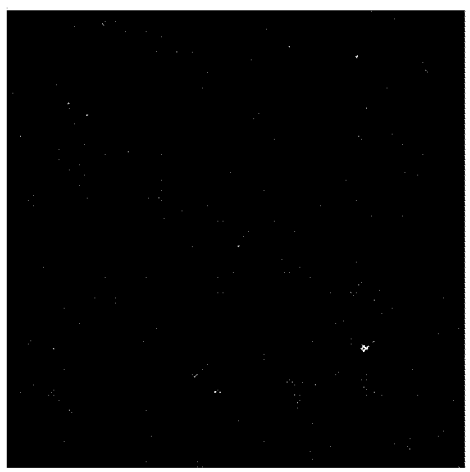

Novel CPPs with improved endosomolytical properties are suggested for in vitro and in vivo applications. The ECP(32-41) composed of 10 amino acid is a CPP of intermediate length containing a heparin binding motif capable of mediating the interaction between ECP and cell surface HSPGs. To identity the minimal sequence requirement for cell-penetrating activity, the C-terminally truncated peptides were synthesized and used to treat Beas-2B cells followed by analysis employing confocal microscopy. FIG. 4 indicated that both ECP(32-41) and ECP(32-41) D1 (SEQ ID NO: 2) entered Beas-2B cells, whereas ECP(32-41)D2 (SEQ ID NO: 3) could not. However, stronger fluorescent signals obtained in the case of ECP(32-41) treatment indicated that 10 amino acids in length were required for efficient cellular uptake.

Example 5

ECP(32-41)-Mediated Protein Delivery

Protein Expression and Purification

For cell-penetration assays, enhanced green fluorescent protein (eGFP) fusion protein was used. The gene fragment encoding eGFP and eGFP-ECP(32-41) was generated using a standard PCR cloning strategy. The fragments encoding eGFP and eGFP-ECP(32-41) were derived from pEGFP-N1 vector (Clontech) using primer sets 5'-CATATGGTGAG-CAAGGGCGAGGAGCTG-3' SEQ ID NO: 26)/5'-CGAGT-GCGGCCGCGAATTCACTTCTTGTACAGCTCGTCA-3' (SEQ ID NO: 27) and 5'-CATATGGTGAGCAAGGGC-GAGGA GCTG-3' (SEQ ID NO: 28)/5'-GAAT-TCAATTTTGGTTTTTGCAACGCCATC-GATAATTCTTCTGTACAGCTCGTCCATG-3' (SEQ ID NO: 29), respectively. The PCR product was individually cloned into the pET-28a plasmid (New England Biolab, Beverly, Mass.) between the NdeI and EcoRI sites to generate recombinant pET-28a-eGFP and pET-28a-eGFP-ECP(32-41) plasmids which were separately used to transform *E. coli* BL21 (DE3) Gold cells (Novagen) for protein expression. Five milliliters of the overnight culture were inoculated into 250 ml of LB containing 100 μg/ml carbenicillin, and grown at 37° C. for 4 h. IPTG was added to a final concentration of 0.5 mM, and the bacteria were harvested 4 h after induction at 20° C. Recombinant eGFP and eGFP-ECP(32-41) fusion protein in the soluble portion of bacterial cell lysates were purified by Ni sepharose affinity column chromatography (GE Healthcare).

Figure 6:
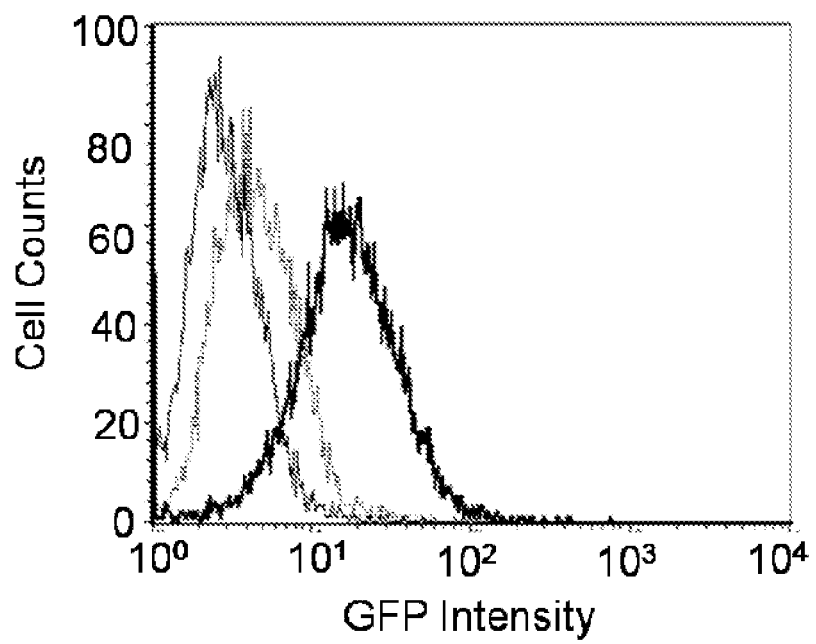
FIG. 6 illustrates in vitro delivery of protein. Beas-2B cells were incubated with 5 μM FITC (control), eGFP or eGFP-ECP(32-41) at 37° C. for 1 h. After treatment, cells were washed with 500 μl PBS and treated with trypsin at 37° C. for 10 min to remove adherent extracellular peptides. The cells were resuspended in 500 μl PBS and analyzed by flow cytometry. The cellular uptake activity was expressed as mean fluorescence intensity (MFI) using FACScalibur (BD Biosciences, Franklin Lakes, N.J.) flow cytometer (FACS). The data represented the means of triplicate incubations.

In a wide sense, CPPs can be described as peptides that have the ability to translocate to the plasma and/or nuclear membrane either alone or together with a desired cargo (Jarver, P., Langel, K., El-Andaloussi, S., and Langel, U. (2007) *Biochem Soc Trans* 35, 770-4). The ability to mediate cellular uptake of a diverse set of cargo is an important characteristic for a CPP to be valuable for applications in biological and biomedical research (Vives, E., Schmidt, J., and Pelegrin, A. (2008) Cell-penetrating and cell-targeting peptides in drug delivery. *Biochim Biophys Acta* 1786, 126-38). Here ECP(32-41)-mediated import of different cargos into cell were demonstrated. First, recombinant Dp2-ECP(32-41) (SEQ ID NO: 5) containing a Dp2 (SEQ ID NO: 4) peptide, the group 2 allergen of *Dermatophagoides pteronyssinus*, was generated. For analysis of cellular uptake, when 5 μM FITC-Dp2 or FITC-Dp2-ECP(32-41) was added to Beas-2B cells and incubated at 37° C. for 30 min, the result showed that only Dp2-ECP(32-41) was able to enter the cells (FIG. 5). Another example of translocation of cargo through ECP(32-41) was enhanced green fluorescence protein (eGFP) of 28 kDa in size. As 5 μM eGFP-ECP(32-41) was added to Beas-2B cells and incubated at 37° C. for 1 h, the internalization of eGFP-ECP(32-41) was monitored by GFP fluorescence and uptake into Beas-2B cells was evidenced by apparent fluorescent signal shift as shown in FIG. 6. For protein cargo delivery, integration of ECP(32-41) sequence has been proven to be feasible and efficient.

Example 6

Intracellular Delivery of a Proapoptotic Peptide

Cell Culture

CHO cells and AGS cells were cultured in F-12 nutrient mixture (Ham's F-12) containing 10% heat-inactivated fetal bovine serum (Gibco, Invitrogen, USA). BEAS-2B cells were cultured in RPMI 1640 medium (Gibco, Invitrogen, USA) supplemented with heat-inactivated 10% (v/v) fetal bovine serum (FBS) (Gibco, Invitrogen, USA), and 1% (v/v) Glutamine-Penicillin-Streptomycin (biosera). A549 cells were cultured in Dulbecco's Modified Eagle Medium (Gibco, Invitrogen, USA) supplemented with heat-inactivated 10% (v/v) fetal bovine serum (FBS) (Gibco, Invitrogen, USA), and 1% (v/v) Glutamine-Penicillin-Streptomycin (biosera). Caco-2 cells were grown in minimum essential medium (MEM; Gibco BRL Life Technologies, Scotland) with 10% v/v fetal bovine serum (FBS), 1% v/v non-essential amino acids (Gibco), 1% v/v L-glutamine (Biowhittaker) and 1% v/v Glutamine-Penicillin-Streptomycin (biosera). All cells were grown on 100-mm dishes and incubated at 37° C. under 5% $CO_2$.

Viability Assay

The cytotoxic effect of peptides on the cell growth were determined by a colorimetric assay using 3-(4,5-dimethylthiazol-2-yl)-2,5-diphenyltetrazolium bromide (MTT) (US Biological, Marblehead, Mass.). Cells were plated in a 96-well plate ($1.0 \times 10^4$ cells/well) and incubated at 37° C. overnight. Each sample was incubated with the indicated concentration (1-100 μM) of peptide. Twenty-four hours after treatment with the indicated peptide, MTT was added, and cell growth was monitored at $A_{570}$ to measure the mitochondrial-dependent formation of a colored product.

A previously reported proapoptotic domain, the peptidomimetic $(KLAKLAK)_2$, (SEQ ID NO: 6) could selectively disrupt negatively charged mitochondrial membranes, but did not interact with eukaryotic cell membranes. Thus, this peptide induced cell death after targeted internalization (Zurita, A. J., Troncoso, P., Cardo-Vila, M., Logothetis, C. J., Pasqualini, R., and Arap, W. (2004) *Cancer Res* 64, 435-9). To evaluate in vitro delivery of a functional peptide, the peptidomimetic drug $(KLAKLAK)_2$ fused with ECP(32-41) was generated by standard solid phase peptide synthesis.

Figure 7:
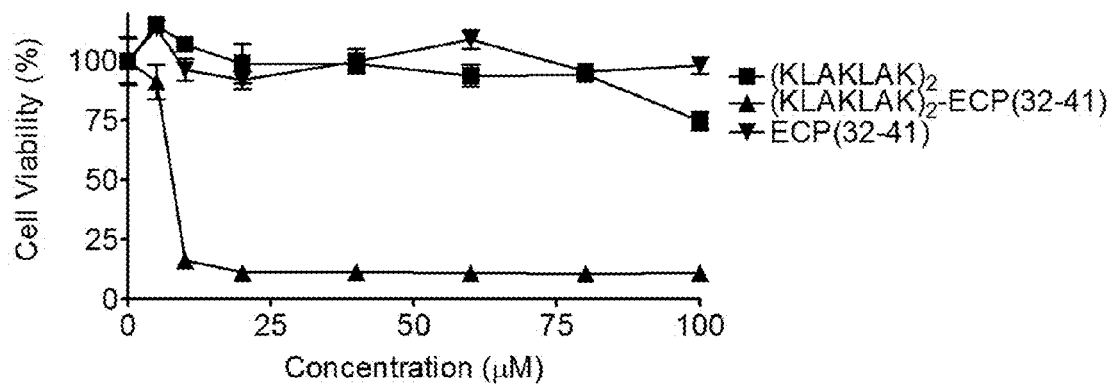
FIG. 7 illustrates in vitro delivery of peptidomimetic drug. (A). Cell viability assay. Beas-2B cells were incubated with 50 μM (KLAKLAK)$_2$-ECP(32-41), ECP(32-41), or (KLAKLAK)$_2$, at 37° C. for 24 h. Effects of (KLAKLAK)$_2$-ECP(32-41) on the cell viability of Beas-2B, A549 and CHO-K1 cells (B), as well as Caco-2 and AGS cells (C). Cell viability in each group was determined by MTT assay and each experiment was performed in triplicate.
Figure 7:
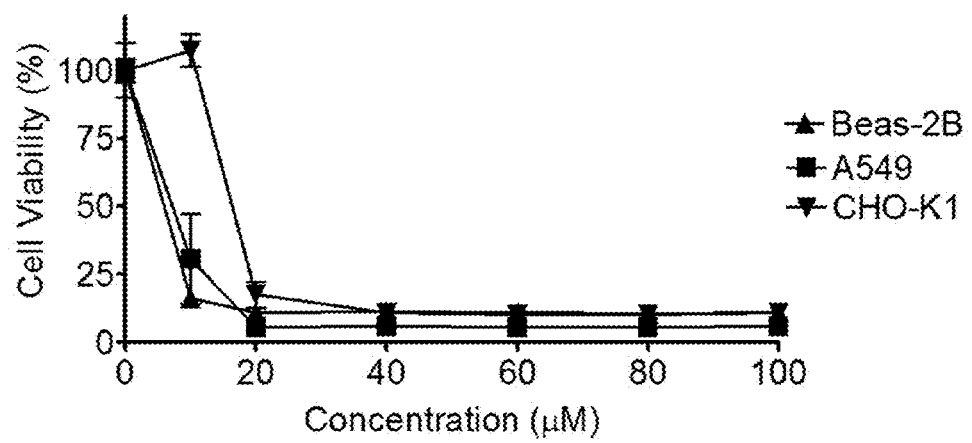
Figure 7:
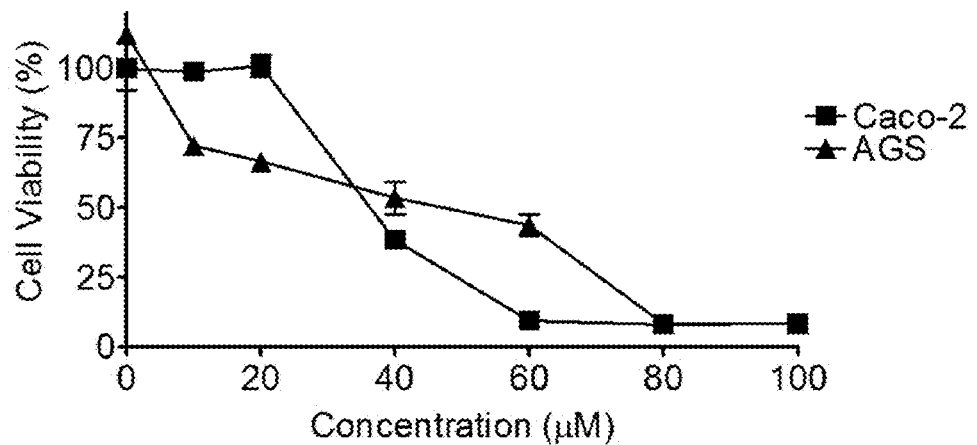

While $(KLAKLAK)_2$ and ECP(32-41) was respectively lacking of cell-penetrating activity and cytotoxicity, the FITC-$(KLAKLAK)_2$-ECP(32-41) (SEQ ID NO: 7) appeared to induce markedly cell death in Beas-2B cells in a concentration-dependent manner (FIG. 7A). The $IC_{50}$ value for $(KLAKLAK)_2$-ECP(32-41) was 7.2 μM.

The effects of FITC-$(KLAKLAK)_2$-ECP(32-41) on cell viability in different cell lines including CHO-K1, A549, Beas-2B, Caco-2 and AGS all showed strong cytotoxicity (FIG. 7B-C). Taken together, in vitro targeted delivery of proapoptotic peptide to cells using ECP(32-41) was demonstrated to be applicable.

Example 7

In Vivo Delivery of ECP(32-41) in Living Organism

In Vivo Delivery

For microinjection, 72 hour-post-fertilization (hpf) zebrafish larva were anesthetized by immersion in water containing 0.17 μg/ml of tricaine (Sigma) and immobilized in 1.2% low-melting agarose gel. The larva were microinjected 4.6 nl of 5 μM FITC or FITC-ECP(32-41) into the blood vessel according to a standard protocol previously described (Levraud, J. P., Colucci-Guyon, E., Redd, M. J., Lutfalla, G, and Herbomel, P. (2008) *Methods Mol Biol* 415, 337-63). The signal of FITC was detected by fluorescence microscopy (Nikon). For direct delivery through culture environment, the 7 day-post-fertilization (dpi) zebrafish larva were soaked in water containing 1 M FITC-ECP(32-41) for 24 h. Then, the zebrafish larva were transferred into freshwater and raised for 2 days prior to observation by fluorescence microscopy (Nikon).

Figure 8:
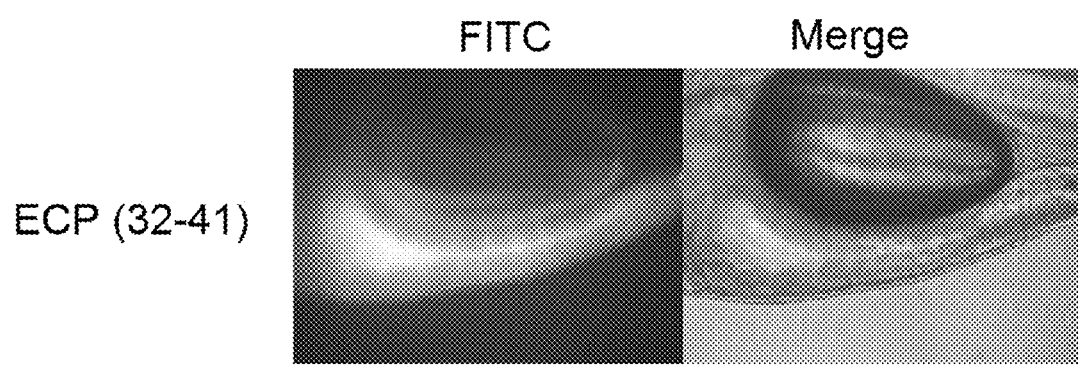
FIG. 8 illustrates in vivo delivery of ECP(32-41). The 72 hour-post-fertilization (hpf) zebrafish larva were microinjected with 4.6 nl of 5 M (A) FITC and observed by fluorescence microscopy (Nikon) at 1 day-post-injection (dpi). (B) FITC-ECP(32-41) delivered by microinjection. The 72 hpf zebrafish larva were microinjected with 4.6 nl of 5 M FITC-ECP(32-41) and observed by fluorescence microscopy (Nikon) at 2 dpi. (C) FITC-ECP(32-41) delivered through culture environment. The 7 day-post-fertilization (dpi) zebrafish larva were soaked in water containing 1 M FITC-ECP(32-41), incubated in freshwater for another 2 days, and then observed by fluorescence microscopy. Figures Magnification fold: (A) 4×, (B) 20×, and (C) 10×.
Figure 8:
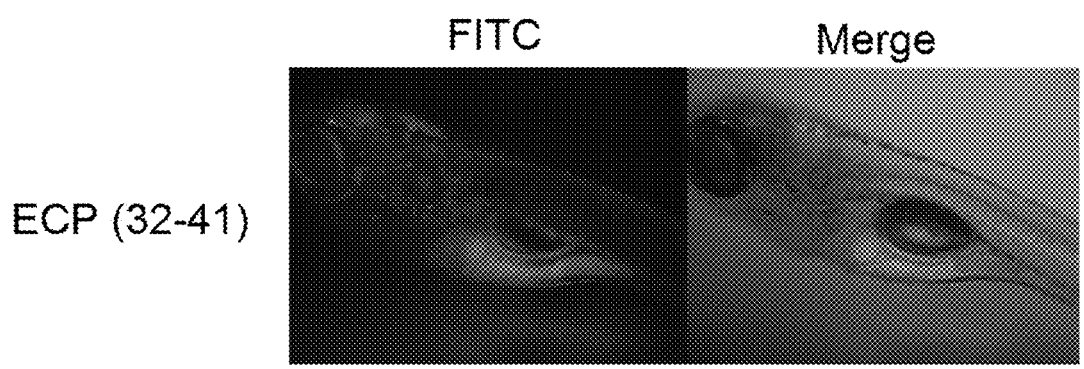

Here zebrafish was used as a model system to examine the delivery of ECP(32-41), 5 μM FITC or FITC-ECP(32-41) was injected into the circulation system of 72 hour-post-fertilization (hpf) zebrafish larva. The fluorescence of FITC alone was almost completely quenched within 24 h after injection (FIG. 8A). Interestingly, the fluorescent FITC-ECP (32-41) signal was clearly detected in the larva 2 days after injection (FIG. 8B). An additional line of evidence for successful in vivo delivery was provided by the following experiment. The 7 day post hatching (dpf) zebrafish larva were soaked in water containing 1 μM FITC-ECP(32-41) for 1 day followed by replacement with fresh water without peptide for two days. Evident fluorescent signal inside the larva was observed in consistent with previous data (FIG. 8C), strongly indicating that ECP(32-41) could delivery fluorescent cargo into a living organism and remained stable for a long time inside zebrafish.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A cell penetrating peptide which consisting of following sequence: $NYBX_1BX_2BNQX_3$, wherein B represents R or K, $X_1$ represents W, A, F, or Y, $X_2$ represents C, and $X_3$ represents N or none.

2. The cell penetrating peptide of claim 1, which is SEQ ID NO: 1.

3. The cell penetrating peptide of claim 1, which is SEQ ID NO: 2.

4. A complex comprising the cell penetrating peptide of claim 1 and a cargo selected from the group consisting of therapeutic agents, diagnostic probes, peptides, nucleic acids, antisense oligonucleotides, proteins, nanoparticles, liposomes, small molecules and radioactive materials.

5. The complex of claim 4, wherein the cargo is selected from chromophores, peptides or proteins.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: ECP(32-41)
<220> FEATURE:
<221> NAME/KEY: PEPTIDE
<222> LOCATION: (1)..(10)
```

```
<400> SEQUENCE: 1

Asn Tyr Arg Trp Arg Cys Lys Asn Gln Asn
1               5                   10

<210> SEQ ID NO 2
<211> LENGTH: 9
<212> TYPE: PRT
<213> ORGANISM: Artificial Sequence
<220> FEATURE:
<223> OTHER INFORMATION: ECP(32-41)D1
<220> FEATURE:
<221> NAME/KEY: PEPTIDE
<222> LOCATION: (1)..(9)

<400> SEQUENCE: 2

Asn Tyr Arg Trp Arg Cys Lys Asn Gln
1               5

<210> SEQ ID NO 3
<211> LENGTH: 8
<212> TYPE: PRT
<213> ORGANISM: Artificial Sequence
<220> FEATURE:
<223> OTHER INFORMATION: ECP(32-41)D2
<220> FEATURE:
<221> NAME/KEY: PEPTIDE
<222> LOCATION: (1)..(8)

<400> SEQUENCE: 3

Asn Tyr Arg Trp Arg Cys Lys Asn
1               5

<210> SEQ ID NO 4
<211> LENGTH: 13
<212> TYPE: PRT
<213> ORGANISM: Artificial Sequence
<220> FEATURE:
<223> OTHER INFORMATION: Dp2
<220> FEATURE:
<221> NAME/KEY: PEPTIDE
<222> LOCATION: (1)..(13)

<400> SEQUENCE: 4

Ile Ile His Arg Gly Lys Pro Phe Gln Leu Glu Ala Val
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Dp2-ECP(32-41)
<220> FEATURE:
<221> NAME/KEY: PEPTIDE
<222> LOCATION: (1)..(23)

<400> SEQUENCE: 5

Ile Ile His Arg Gly Lys Pro Phe Gln Leu Glu Ala Val Asn Tyr Arg
1               5                   10                  15

Trp Arg Cys Lys Asn Gln Asn
            20

<210> SEQ ID NO 6
<211> LENGTH: 14
<212> TYPE: PRT
<213> ORGANISM: Artificial Sequence
<220> FEATURE:
<223> OTHER INFORMATION: (KLAKLAK)2
<220> FEATURE:
```

```
<221> NAME/KEY: PEPTIDE
<222> LOCATION: (1)..(14)

<400> SEQUENCE: 6

Lys Leu Ala Lys Leu Ala Lys Lys Leu Ala Lys Leu Ala Lys
1               5                   10

<210> SEQ ID NO 7
<211> LENGTH: 24
<212> TYPE: PRT
<213> ORGANISM: Artificial Sequence
<220> FEATURE:
<223> OTHER INFORMATION: (KLAKLAK)2-ECP(32-41)
<220> FEATURE:
<221> NAME/KEY: PEPTIDE
<222> LOCATION: (1)..(24)

<400> SEQUENCE: 7

Lys Leu Ala Lys Leu Ala Lys Lys Leu Ala Lys Leu Ala Lys Asn Tyr
1               5                   10                  15

Arg Trp Arg Cys Lys Asn Gln Asn
            20

<210> SEQ ID NO 8
<211> LENGTH: 34
<212> TYPE: DNA
<213> ORGANISM: Artificial Sequence
<220> FEATURE:
<223> OTHER INFORMATION: (R34A) forward primer
<220> FEATURE:
<221> NAME/KEY: misc_feature
<222> LOCATION: (1)..(34)

<400> SEQUENCE: 8
gcaattaaca attatgcatg gcgttgcaaa aacc                           34

<210> SEQ ID NO 9
<211> LENGTH: 34
<212> TYPE: DNA
<213> ORGANISM: Artificial Sequence
<220> FEATURE:
<223> OTHER INFORMATION: (R34A) reverse primer
<220> FEATURE:
<221> NAME/KEY: misc_feature
<222> LOCATION: (1)..(34)

<400> SEQUENCE: 9 ggttttttgca acgccatgca taattgttaa ttgc                          34

<210> SEQ ID NO 10
<211> LENGTH: 34
<212> TYPE: DNA
<213> ORGANISM: Artificial Sequence
<220> FEATURE:
<223> OTHER INFORMATION: (R34K) forward primer
<220> FEATURE:
<221> NAME/KEY: misc_feature
<222> LOCATION: (1)..(34)

<400> SEQUENCE: 10
gcaattaaca attataaatg gcgttgcaaa aacc                           34

<210> SEQ ID NO 11
<211> LENGTH: 34
<212> TYPE: DNA
<213> ORGANISM: Artificial Sequence
<220> FEATURE:
<223> OTHER INFORMATION: (R34K) reverse primer
<220> FEATURE:
```

<221> NAME/KEY: misc_feature
<222> LOCATION: (1)..(34)

<400> SEQUENCE: 11
ggtttttgca acgccattta taattgttaa ttgc        34

<210> SEQ ID NO 12
<211> LENGTH: 31
<212> TYPE: DNA
<213> ORGANISM: Artificial Sequence
<220> FEATURE:
<223> OTHER INFORMATION: (W35A) forward primer
<220> FEATURE:
<221> NAME/KEY: misc_feature
<222> LOCATION: (1)..(31)

<400> SEQUENCE: 12
attaacaatt atcgagcgcg ttgcaaaaac c        31

<210> SEQ ID NO 13
<211> LENGTH: 31
<212> TYPE: DNA
<213> ORGANISM: Artificial Sequence
<220> FEATURE:
<223> OTHER INFORMATION: (W35A) reverse primer
<220> FEATURE:
<221> NAME/KEY: misc_feature
<222> LOCATION: (1)..(31)

<400> SEQUENCE: 13
ggtttttgca acgcgctcga taattgttaa t        31

<210> SEQ ID NO 14
<211> LENGTH: 31
<212> TYPE: DNA
<213> ORGANISM: Artificial Sequence
<220> FEATURE:
<223> OTHER INFORMATION: (W35F) forward primer
<220> FEATURE:
<221> NAME/KEY: misc_feature
<222> LOCATION: (1)..(31)

<400> SEQUENCE: 14
attaacaatt atcgatttcg ttgcaaaaac c        31

<210> SEQ ID NO 15
<211> LENGTH: 31
<212> TYPE: DNA
<213> ORGANISM: Artificial Sequence
<220> FEATURE:
<223> OTHER INFORMATION: (W35F) reverse primer
<220> FEATURE:
<221> NAME/KEY: misc_feature
<222> LOCATION: (1)..(31)

<400> SEQUENCE: 15
ggtttttgca acgaaatcga taattgttaa t        31

<210> SEQ ID NO 16
<211> LENGTH: 31
<212> TYPE: DNA
<213> ORGANISM: Artificial Sequence
<220> FEATURE:
<223> OTHER INFORMATION: (W35Y) forward primer
<220> FEATURE:
<221> NAME/KEY: misc_feature
<222> LOCATION: (1)..(31)

<400> SEQUENCE: 16
attaacaatt atcgatctcg ttgcaaaaac c                                    31

<210> SEQ ID NO 17
<211> LENGTH: 31
<212> TYPE: DNA
<213> ORGANISM: Artificial Sequence
<220> FEATURE:
<223> OTHER INFORMATION: (W35Y) reverse primer
<220> FEATURE:
<221> NAME/KEY: misc_feature
<222> LOCATION: (1)..(31)

<400> SEQUENCE: 17
ggtttttgca acgagatcga taattgttaa t                                    31

<210> SEQ ID NO 18
<211> LENGTH: 33
<212> TYPE: DNA
<213> ORGANISM: Artificial Sequence
<220> FEATURE:
<223> OTHER INFORMATION: (R36A) forward primer
<220> FEATURE:
<221> NAME/KEY: misc_feature
<222> LOCATION: (1)..(33)

<400> SEQUENCE: 18
caattatcga tgggcttgca aaaccaaaa tac                                   33

<210> SEQ ID NO 19
<211> LENGTH: 33
<212> TYPE: DNA
<213> ORGANISM: Artificial Sequence
<220> FEATURE:
<223> OTHER INFORMATION: (R36A) reverse primer
<220> FEATURE:
<221> NAME/KEY: misc_feature
<222> LOCATION: (1)..(33)

<400> SEQUENCE: 19
gtattttggt ttttgcaagc ccatcgataa ttg                                  33

<210> SEQ ID NO 20
<211> LENGTH: 33
<212> TYPE: DNA
<213> ORGANISM: Artificial Sequence
<220> FEATURE:
<223> OTHER INFORMATION: (R36K) forward primer
<220> FEATURE:
<221> NAME/KEY: misc_feature
<222> LOCATION: (1)..(33)

<400> SEQUENCE: 20
caattatcga tggaaatgca aaaccaaaa tac                                   33

<210> SEQ ID NO 21
<211> LENGTH: 33
<212> TYPE: DNA
<213> ORGANISM: Artificial Sequence
<220> FEATURE:
<223> OTHER INFORMATION: (R36K) reverse primer
<220> FEATURE:
<221> NAME/KEY: misc_feature
<222> LOCATION: (1)..(33)

<400> SEQUENCE: 21
gtattttggt ttttgcaatt tcatcgataa ttg                                  33

<210> SEQ ID NO 22
<211> LENGTH: 30

```
<212> TYPE: DNA
<213> ORGANISM: Artificial Sequence
<220> FEATURE:
<223> OTHER INFORMATION: (K38A) forward primer
<220> FEATURE:
<221> NAME/KEY: misc_feature
<222> LOCATION: (1)..(30)

<400> SEQUENCE: 22
tatcgatggc gttgcgcaaa ccaaaatact                               30

<210> SEQ ID NO 23
<211> LENGTH: 31
<212> TYPE: DNA
<213> ORGANISM: Artificial Sequence
<220> FEATURE:
<223> OTHER INFORMATION: (K38A) reverse primer
<220> FEATURE:
<221> NAME/KEY: misc_feature
<222> LOCATION: (1)..(31)

<400> SEQUENCE: 23
aaagtatttt ggtttgcgca acgccatcga t                             31

<210> SEQ ID NO 24
<211> LENGTH: 30
<212> TYPE: DNA
<213> ORGANISM: Artificial Sequence
<220> FEATURE:
<223> OTHER INFORMATION: (K38R) forward primer
<220> FEATURE:
<221> NAME/KEY: misc_feature
<222> LOCATION: (1)..(30)

<400> SEQUENCE: 24
tatcgatggc gttgcaaaaa ccaaaatact                               30

<210> SEQ ID NO 25
<211> LENGTH: 31
<212> TYPE: DNA
<213> ORGANISM: Artificial Sequence
<220> FEATURE:
<223> OTHER INFORMATION: (K38R) reverse primer
<220> FEATURE:
<221> NAME/KEY: misc_feature
<222> LOCATION: (1)..(31)

<400> SEQUENCE: 25
aaagtatttt ggttttttgca acgccatcga t                            31

<210> SEQ ID NO 26
<211> LENGTH: 27
<212> TYPE: DNA
<213> ORGANISM: Artificial Sequence
<220> FEATURE:
<223> OTHER INFORMATION: (eGFP) forward primer
<220> FEATURE:
<221> NAME/KEY: misc_feature
<222> LOCATION: (1)..(27)

<400> SEQUENCE: 26
catatggtga gcaagggcga ggagctg                                  27

<210> SEQ ID NO 27
<211> LENGTH: 39
<212> TYPE: DNA
<213> ORGANISM: Artificial Sequence
<220> FEATURE:
<223> OTHER INFORMATION: (eGFP) reverse primer
<220> FEATURE:
```

-continued

```
<221> NAME/KEY: misc_feature
<222> LOCATION: (1)..(39)

<400> SEQUENCE: 27
cgagtgcggc cgcgaattca cttcttgtac agctcgtca                        39

<210> SEQ ID NO 28
<211> LENGTH: 27
<212> TYPE: DNA
<213> ORGANISM: Artificial Sequence
<220> FEATURE:
<223> OTHER INFORMATION: eGFP-ECP(32-41) forward primer
<220> FEATURE:
<221> NAME/KEY: misc_feature
<222> LOCATION: (1)..(27)

<400> SEQUENCE: 28
catatggtga gcaagggcga ggagctg                                     27

<210> SEQ ID NO 29
<211> LENGTH: 58
<212> TYPE: DNA
<213> ORGANISM: Artificial Sequence
<220> FEATURE:
<223> OTHER INFORMATION: eGFP-ECP(32-41) reverse primer
<220> FEATURE:
<221> NAME/KEY: misc_feature
<222> LOCATION: (1)..(58)

<400> SEQUENCE: 29
gaattcaatt ttggtttttg caacgccatc gataattctt ctgtacagct cgtccatg      58
```